United States Patent
Hamasaki

(10) Patent No.: US 10,578,529 B2
(45) Date of Patent: Mar. 3, 2020

(54) TENSION MEASUREMENT DEVICE

(71) Applicant: BANDO CHEMICAL INDUSTRIES, LTD., Kobe-shi, Hyogo (JP)

(72) Inventor: Yuta Hamasaki, Kobe (JP)

(73) Assignee: BANDO CHEMICAL INDUSTRIES, LTD., Hyogo (JP)

( * ) Notice: Subject to any disclaimer, the term of this patent is extended or adjusted under 35 U.S.C. 154(b) by 0 days.

(21) Appl. No.: 16/574,411

(22) Filed: Sep. 18, 2019

(65) Prior Publication Data

US 2020/0011776 A1    Jan. 9, 2020

Related U.S. Application Data

(63) Continuation of application No. PCT/JP2017/045337, filed on Dec. 18, 2017.

(30) Foreign Application Priority Data

Mar. 22, 2017  (JP) .................. 2017-055606

(51) Int. Cl.
 *G01N 3/28*    (2006.01)
 *G01N 3/08*    (2006.01)
 *G01N 3/30*    (2006.01)

(52) U.S. Cl.
 CPC .......... *G01N 3/08* (2013.01); *G01N 3/28* (2013.01); *G01N 3/30* (2013.01)

(58) Field of Classification Search
 CPC ............... G01N 3/08; G01N 3/28; G01N 3/12

USPC ............................................ 73/831
See application file for complete search history.

(56) References Cited

U.S. PATENT DOCUMENTS

2017/0115173 A1*  4/2017  Miyata ............... G01L 5/10

FOREIGN PATENT DOCUMENTS

| JP | S53-116757 U1 | 9/1978 |
| JP | S55-103428 A  | 8/1980 |
| JP | H09-203657 A  | 8/1997 |
| JP | 2016-151431 A | 8/2016 |

OTHER PUBLICATIONS

ISR in PCT application No. PCT/JP2017/045337 dated Jan. 16, 2018.
Written Opinion in PCT application No. PCT/JP2017/045337 dated Jan. 16, 2018.

* cited by examiner

*Primary Examiner* — Tarun Sinha
(74) *Attorney, Agent, or Firm* — Maschoff Brennan

(57) ABSTRACT

In a tension measurement device, a load cell, a base portion in which the load cell is provided, a pair of load transfer beams each having a support point and an action point provided in different positions and being configured to transfer a load to the load cell at a tip side, and a pressing member which is supported by the base side pins of the pair of load transfer beams and to which the load is applied are provided.

10 Claims, 9 Drawing Sheets

TENSION MEASUREMENT DEVICE

CROSS-REFERENCE TO RELATED APPLICATIONS

This is a continuation of International Application No. PCT/JP2017/045337 filed on Dec. 18, 2017, which claims priority to Japanese Patent Application No. 2017-055606 filed on Mar. 22, 2017. The entire disclosures of these applications are incorporated by reference herein.

BACKGROUND

The present disclosure relates to a tension measurement device that includes a load measurement device that measures a load applied to a pressing member using the principle of leverage and is configured such that a subject member to be measured, such as a belt or the like, is clamped between a pair of support rollers and a pressing member and thereby a tension can be measured.

Conventionally, in a case in which a three-point tension meter is used, a structure in which a load detection section (a load sensor) is disposed in only one position at a center of a pressing section in a longitudinal direction is employed in many cases. However, in the structure in which the load detection section is provided in only one position at the center of the pressing section, when a target to be measured is shifted from the center in the longitudinal direction, a load applied to the load detection section is shifted from an intended load direction, and therefore, a load that is a smaller value than a true value is detected in some cases.

Thus, for example, as described in Japanese Unexamined Patent Publication No. 2016-151431, a structure in which a sliding direction is regulated to be one direction such that movement of the pressing section is perpendicular to the load detection section is needed. Specifically, a structure in which a boss portion and a through hole through which the boss portion passes are provided and a fit-in gap therebetween is made small such that the pressing section moves only in one direction is needed.

SUMMARY

However, in a method disclosed in Japanese Unexamined Patent Publication No. 2016-151431, unless a gap of a fitting portion is made very small, biting due to an inclination of the fitting portion occurs when a biased load is applied, so that the pressing section does not slide, and therefore, a clearance design of the fitting portion is difficult.

Also, a member, such as, for example, a slide rail, which is a mechanism that moves with high accuracy in one direction can be used, but a problem arises in which a structure is very complicated and expensive.

In view of the above described points, the present disclosure has been devised and it is therefore an object of the present disclosure to reduce a biased load applied to a load detection section depending on a setting position of a subject member to be measured in a relatively simple structure.

To achieve the above described object, according to the present disclosure, a load from a pressing member is transferred to a load sensor via a pair of load transfer beams.

Specifically, according to a first aspect of the present disclosure, a tension measurement device includes a load sensor, a base portion in which the load sensor is provided, a pair of load transfer beams each having a support point and an action point provided in different positions and being configured to transfer a load to the load sensor at a tip side, and a pressing member which is supported by the action points of the pair of load transfer beams and to which the load is applied, and a pair of rotatable first support rollers disposed at both sides of the pressing member, and a subject member to be measured is clamped between the pair of first support rollers and the pressing member, and thereby, a tension can be measured.

In the above described configuration, even when a load position in which a load is applied to the pressing member is shifted from the load sensor, the load is indirectly transferred to the load sensor via the pair of load transfer beams, and therefore, a measurement error is reduced by effects of two leverages. Thus, a highly accurate tension measurement device in which a biased load applied to the load detection section depending on a setting position of the subject member to be measured is reduced can be achieved.

According to a second aspect of the present disclosure, in the first aspect, the pair of load transfer beams has a plate-like shape and is supported by base side pins with respect to the base portion at support points.

In the above described configuration, the load is reliably transferred by the pair of load transfer beams in a narrow space.

According to a third aspect of the present disclosure, in the second aspect, the pressing member is supported by the pair of load transfer beams via pressing side pins at the action points.

In the above described configuration, the load is transferred via the pressing side pins, and therefore, a linear motion structure is not needed and a space-saving structure can be achieved.

According to a fourth aspect of the present disclosure, in the third aspect, tips of the pair of load transfer beams overlap with one another via a beam side pin and one of the tips abuts on a load detection section of the load sensor.

In the above described configuration, the load applied to the pair of load transfer beams in the narrow space is reliably transferred to the load sensor.

According to a fifth aspect of the present disclosure, in the fourth aspect, each of the base side pins, the pressing side pins, and the beam side pin fits in a corresponding one of recessed portions formed in the base portion, the pressing member, or the load transfer beams.

In the above described configuration, each pin is not displaced, and therefore, the load can be reliably transferred and assembling is simplified.

According to a sixth aspect of the present disclosure, in the fourth or fifth aspect, the pair of base side pins, the pair of pressing side pins, and the beam side pin are disposed symmetrically about the load detection section of the load sensor as a center.

In the above described configuration, the load applied to the load sensor can be reduced to be smaller than an actual load and a ratio at which the load is reduced can be arbitrarily selected.

According to a seventh aspect of the present disclosure, in any one of the fourth to sixth aspects, the pair of base side pins, the pair of pressing side pins, and the beam side pin are disposed so as to be aligned in parallel.

In the above described configuration, the load is accurately transferred from the pressing member to the load sensor.

A tension measurement device according to an eight aspect of the present disclosure further includes, in any one of the first to seventh aspects, a pair of rotatable second support rollers in positions opposed to the pair of first support rollers, the pressing member projects toward the pair of first support rollers from a line connecting the pair of second support rollers, and a positional relationship between the pressing member and the pair of second support rollers is fixed.

In the above described configuration, the pair of second support rollers is provided in positions opposed to the pair of first support rollers that support the subject member to be measured, the subject member to be measured is clamped by both of the support rollers, and therefore, even when a thickness of the subject member to be measured is changed, a contact angle is hardly changed and variations of a tension can be reduced. Also, the pressing member is configured to properly project, and thereby, a tension can be measured based on a component force applied to the pressing member. A positional relationship between the pressing member and the pair of second support rollers is fixed, and thereby, even when the thickness of the subject member to be measured is changed, the contact angle of the pressing member with respect to the subject member to be measured is hardly changed. Therefore, the tension of the subject member to be measured can be accurately measured. The term "fixed" as used herein does not mean that the positional relationship cannot be changed at all, but has a meaning including a case in which the positional relationship is changed depending on cases, and thereafter, the changed positional relationship is fixed.

In a ninth aspect of the present disclosure, in the eighth aspect, the pair of first support rollers is rotatably supported by a first case, the pair of second support rollers is rotatably supported by a second case, the base portion, the pair of load transfer beams, and the pressing member are provided in the second case, and the subject member to be measured is clamped by the first case and the second case, and thereby, a tension of the subject member to be measured can be measured.

In the above described configuration, it is not needed to have the subject member to be measured pass between the rollers, and therefore, the subject member to be measured can be clamped by the first case and the second case with the subject member to be measured set, thereby easily performing tension measurement.

According to a tenth aspect of the present disclosure, in the ninth aspect, the subject member to be measured is a fastening belt and, in a state in which an object is fastened by the fastening belt, the fastening belt is clamped between the first case and the second case, and thereby, a tension of the fastening belt can be measured.

In the above described configuration, the tension of the fastening belt can be measured while the fastening belt is fastened, and tension management is very easy.

As has been described above, according to the present disclosure, a pair of load transfer beams each having a support point and an action point provided in different positions and being configured to transfer a load to the load sensor at a tip side, and a pressing member which is supported by the action points of the pair of load transfer beams and to which the load is applied are provided, and thereby, a biased load to a load detection section depending on a setting position of a subject member to be measured can be reduced using the principle of leverage and a measurement error can be reduced in a relatively simple configuration.

DETAILED DESCRIPTION

Figure 1:
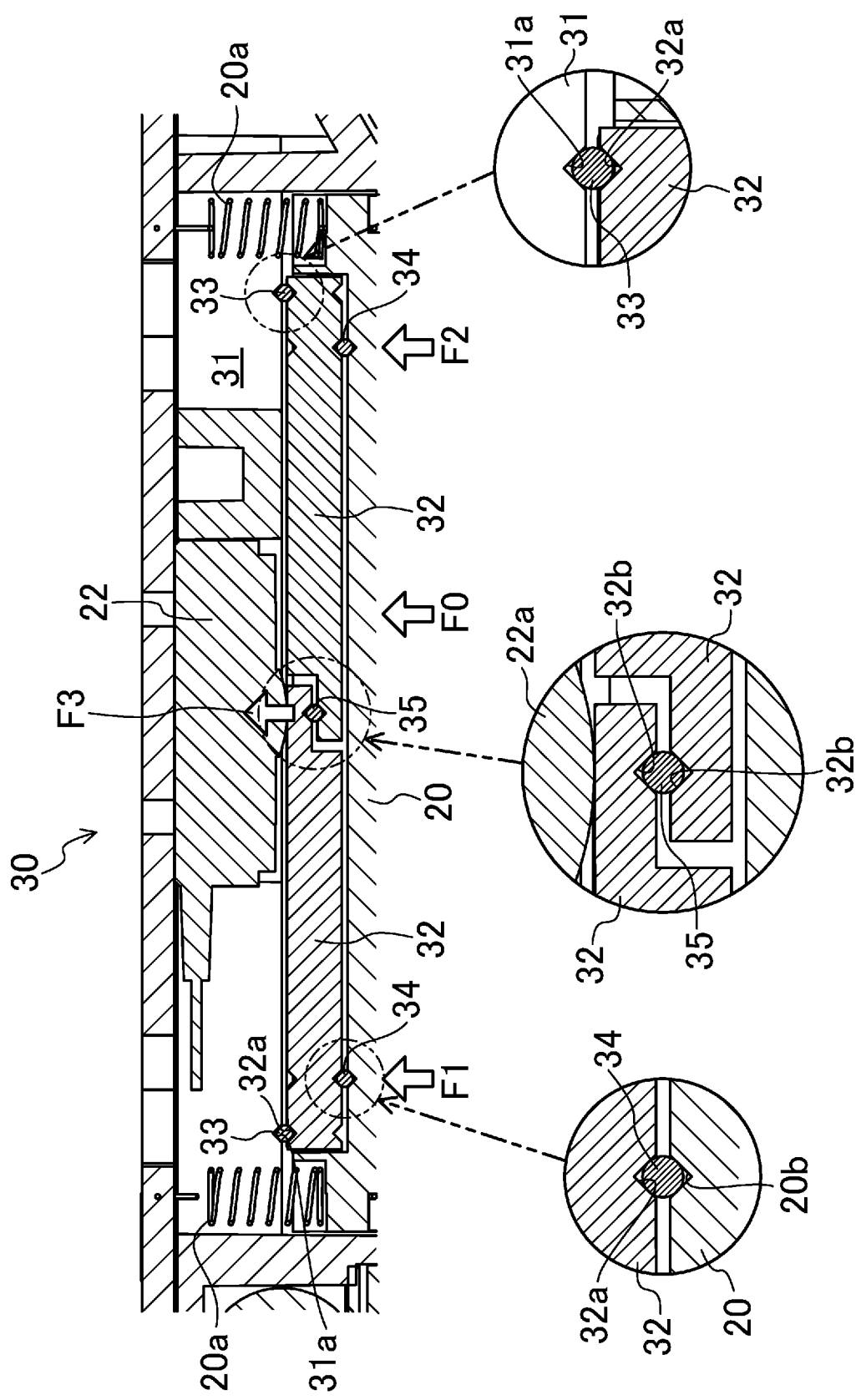
FIG. 1 is an enlarged cross-sectional view illustrating an I portion of FIG. 8 according to an embodiment of the present disclosure.
Figure 2:
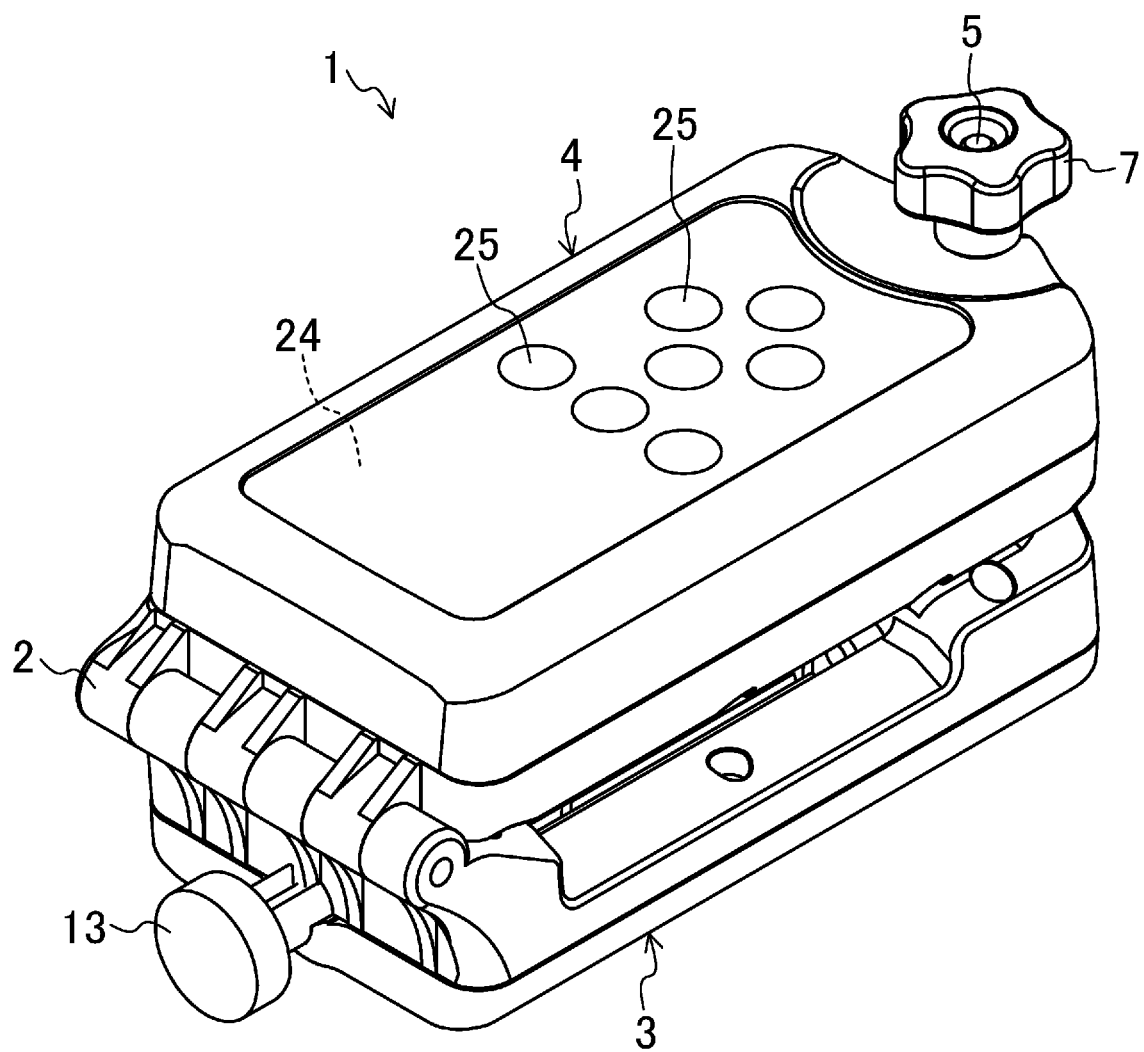
FIG. 2 is a perspective view illustrating a tension measurement device.
Figure 3:
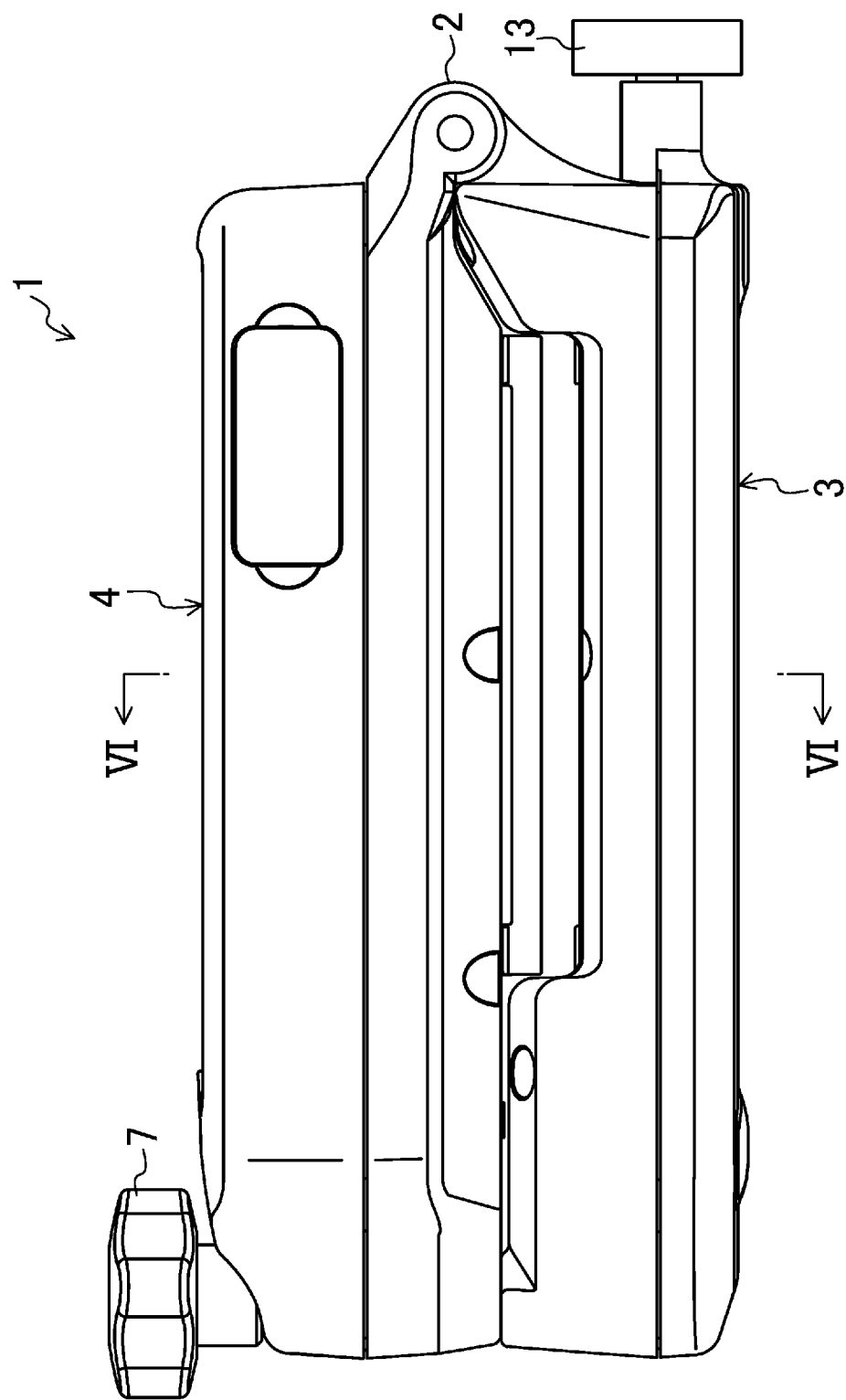
FIG. 3 is a front view illustrating the tension measurement device.

Embodiments of the present disclosure will be described with reference to the accompanying drawings.

FIG. 2 to FIG. 5 and FIG. 8 illustrate a tension measurement device 1 including a load measurement device 30 mounted therein according to an embodiment of the present disclosure, and the tension measurement device 1 includes a first case 3 and a second case 4 that are jointed to one another through a hinge portion 2 serving as a center so as to be openable and closable. The hinge portion 2 may have any structure as long as the structure is a general hinge structure.

Figure 6:
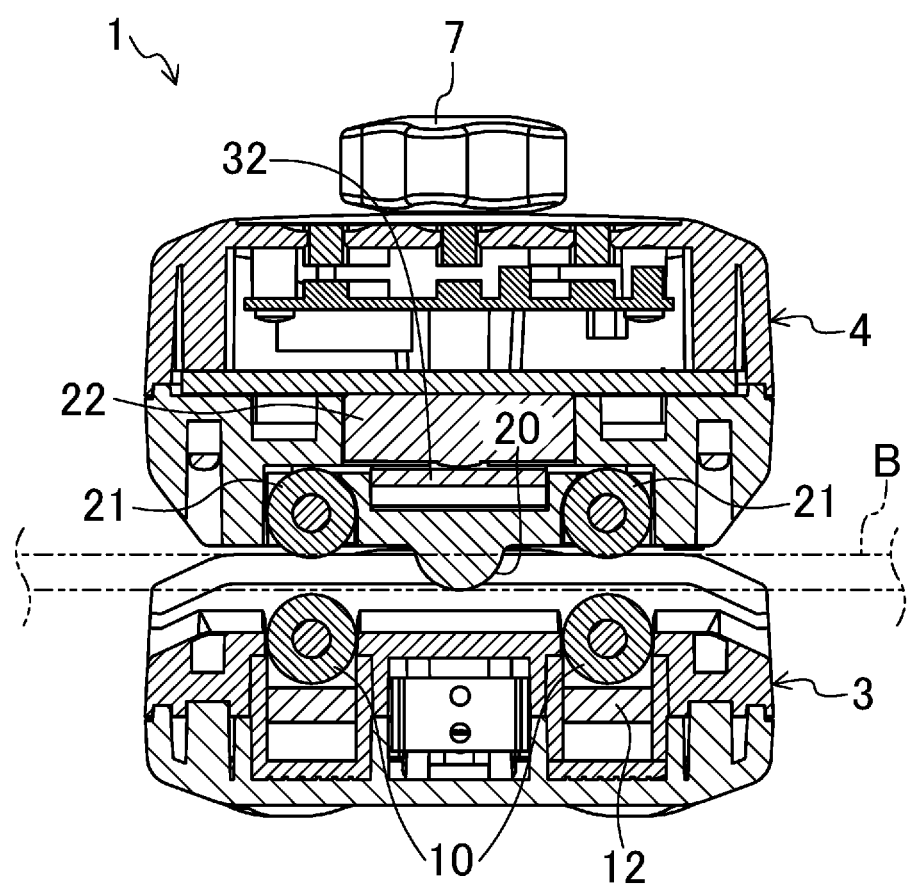
FIG. 6 is a cross-sectional view taken along a line VI-VI of FIG. 3.
Figure 8:
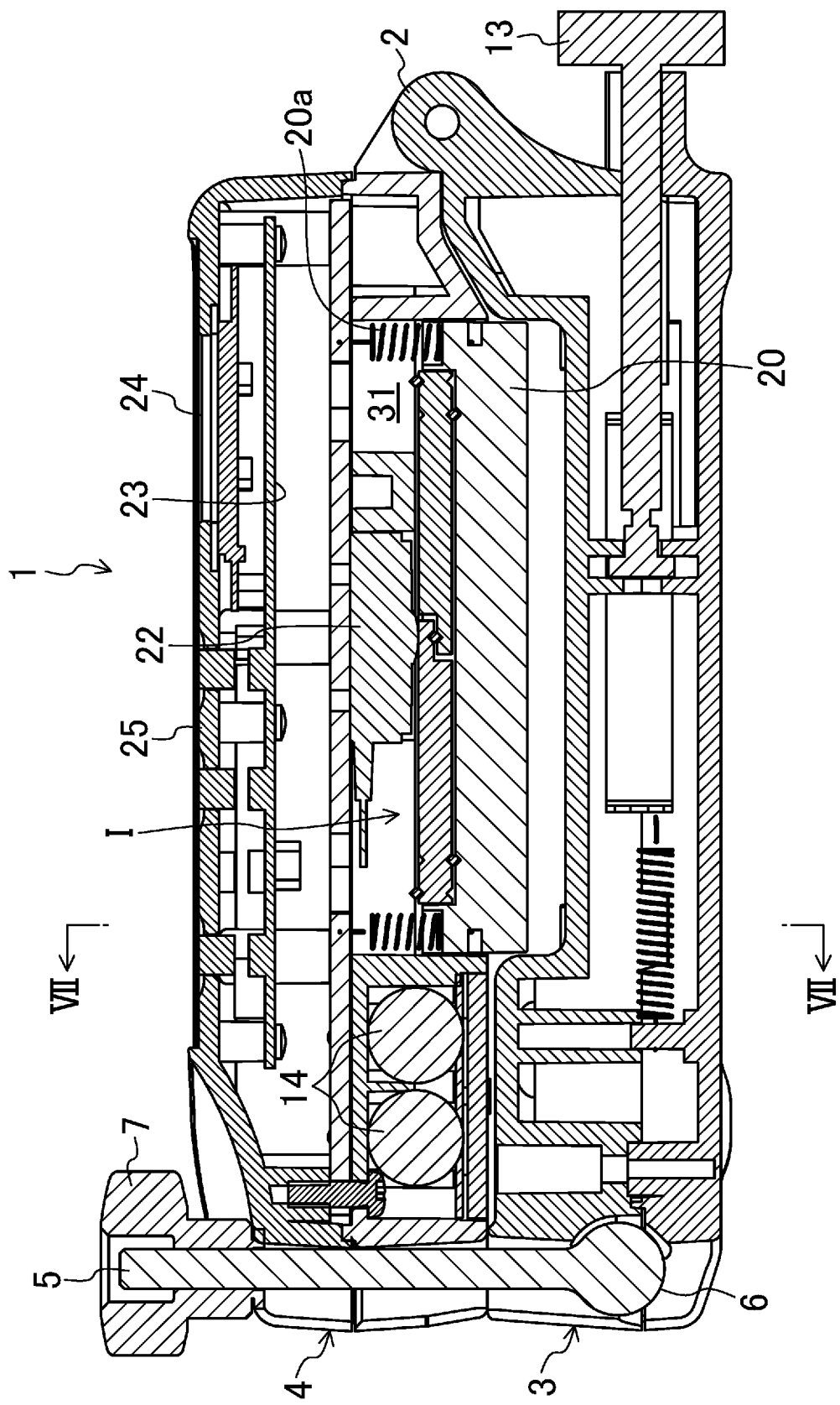
FIG. 8 is a cross-sectional view taken along a line VIII-VIII of FIG. 5.

As illustrated in FIG. 6, a pair of rotatable first support rollers 10 is provided in the first case 3. For example, an outer diameter of the first support rollers 10 is 12 mm and the first support rollers 10 are provided in parallel to one another with a space of, for example, 40 mm therebetween. The first support rollers 10 may be made of metal and may be made resin and both ends of each of the first support rollers 10 are rotatably supported by the first case 3. Although not illustrated in detail, each of the pair of first support rollers 10 is rotatably supported by a plate-like roller support member 12 and the roller support member 12 is housed in the first case 3 so as to be movable in an up-down direction in a state in which the roller support member 12 is biased toward the second case 4 by a pair of compression coil springs provided in the first case 3. As illustrated in FIG. 8, the roller support member 12 is configured to move up and down by operating a tightening adjustment section 13 provided in the first case 3.

A pressing member 20 is provided so as to be disposed in a position opposed to a center between the pair of first support rollers 10 in the second case 4. The pressing member 20 has a curved surface having, for example, a same outer diameter (12 mm) as that of the first support rollers 10 and is made of, for example, a resin material or a metal material which has excellent slidability, although the pressing member 20 itself does not rotate. The pressing member 20 is built in so as to be pushed back toward the second case 4 by a predetermined force by a support spring 20a and be locked.

As illustrated in FIG. 6, in positions opposed to the pair of first support rollers 10 in the second case 4, a pair of rotatable second support rollers 21 is disposed in parallel to one another with the pressing member 20 interposed therebetween. For example, the second support rollers 21 are rollers each of which has the same outer diameter (12 mm) as that of the first support rollers 10, for example, with a space of 40 mm therebetween, and both ends of each of the second support rollers 21 is rotatably supported by the second case 4.

As illustrated in FIG. 8, a load cell 22 as a load sensor that can measure a load that is generated in the pressing member 20 is built in in the second case 4. The load cell 22 is connected to a circuit board 23 provided in the second case 4. Also, a display section 24 that can display a measurement result measured by the load cell 22 and an operation section 25 that performs measurement by the load cell 22 are provided in the second case 4. Each of the display section 24 and the operation section 25 is connected to the circuit board 23. Also, a battery 14 that supplies power to the load cell 22, the display section 24, and the circuit board 23 can be housed in the second case 4. Note that the battery 14 may be provided in the first case 3.

Figure 7:
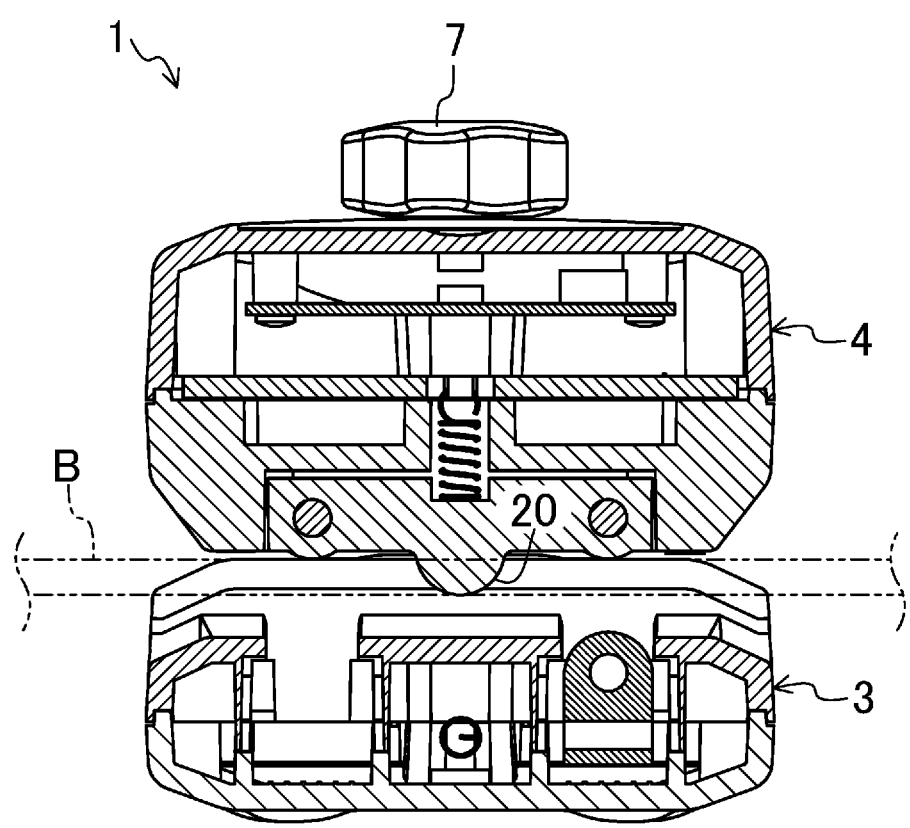
FIG. 7 is a cross-sectional view taken along a line VII-VII of FIG. 5.

By forming the above described structure, the tension measurement device 1 is configured such that a subject member to be measured is clamped between the pair of the first support rollers 10 and the pressing member 20, and thereby, a tension thereof can be measured. The subject member to be measured is, for example, a fastening belt B, as illustrated by imaginary lines in FIG. 6 and FIG. 7, and a width and a thickness of the fastening belt B differ depending on a subject to be fixed (a subject to be transferred) that is fixed to a deck of a ship or the like.

As illustrated in FIG. 6, the pressing member 20 projects toward the pair of first support rollers 10 from a line connecting the pair of the second support rollers 21 by a predetermined amount. This projection amount has to be a proper amount, not a too large amount, in order to reduce reduction in tension when the tension measurement device 1 is removed after measuring. By forming the above described structure, a positional relationship between the pressing member 20 and the pair of second support rollers 21 is fixed. Note that the pressing member 20 may be configured such that the projection amount is changeable and, after the projection amount is changed, the positional relationship between the pair of second support rollers 21 and the pressing member 20 may be set fixed until next change is made.

Figure 4:
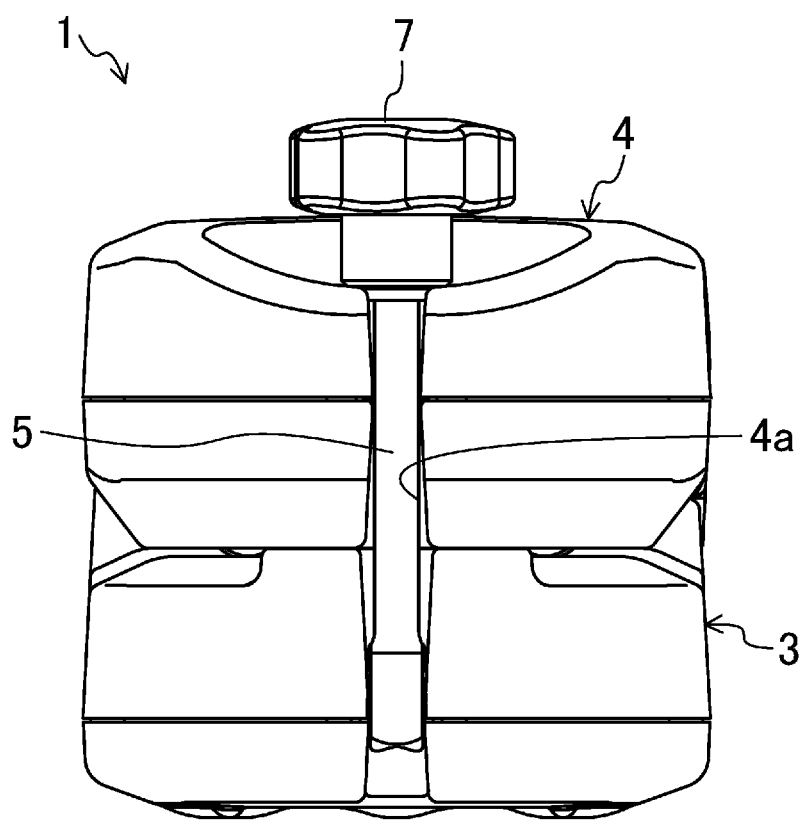
FIG. 4 is a left side view illustrating the tension measurement device.
Figure 5:
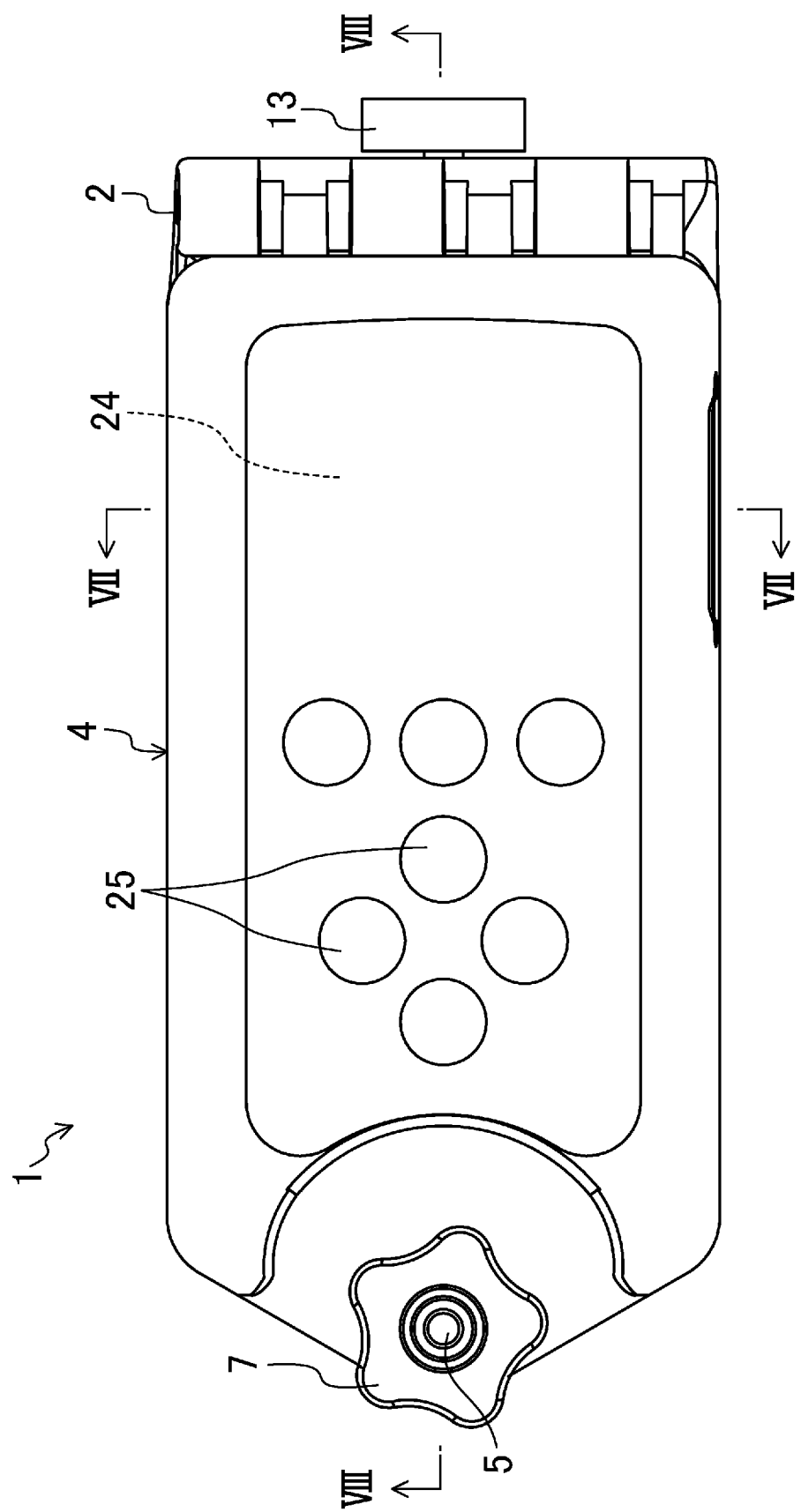
FIG. 5 is a plan view illustrating the tension measurement device.

Also, as illustrated in FIG. 4 and FIG. 8, a clamping rod 5 is provided on an opposite side to the hinge portion 2 of the first case 3 so as to be slidable with a sliding axis 6 serving as a center. A rod housing section 4a that can house the clamping rod 5 is recessed in the second case 4. A knob 7 is provided at a tip of the clamping rod 5 and the fastening belt B can be clamped between the first case 3 and the second d case 4 with a proper force by tightening the knob 7. For example, the fastening belt B is clamped by the first case 3 and the second case 4, and thereby, a tension of the fastening belt B can be measured by the load cell 22, can be displayed by the display section 24, and can be recorded in the circuit board 23 or the like.

Next, the load measurement device 30 of this embodiment will be described in detail.

As illustrated in FIG. 1, the load cell 22 including a load sensor is supported to be fixed to a base portion 31 formed of a portion of the second case 4. A pair of load transfer beams 32 that transfer a load to the load cell 22 at a tip side is provided in a vicinity of a load action position (a load detection section 22a) of the load cell 22. The pair of load transfer beams 32 is configured such that base sides of the load transfer beams 32 abut on (are supported by) base side pins 33 as support points provided in different positions and pressing side pins 34 as action points are provided on positions closer to tip sides than the base side pins 33. The pressing member 20 to which a load is applied abuts on (is supported by) the pressing side pins 34 of the pair of load transfer beams 32.

The pair of load transfer beams 32 has, for example, a plate-like shape and abuts on (is supported by) a corresponding one of the base side pins 33 each of which is a support point with respect to the base portion 31 and has a rod-like shape. The pressing member 20 abuts on (is supported by) the pair of load transfer beams 32 via the pressing side pins 34 each having a rod-like shape at action points. Tips of the pair of load transfer beams 32 overlap one anther via a beam side pin 35 having a rod-like shape and one of the tips abuts on the load detection section 22a of the load cell 22.

The base side pins 33, the pressing side pins 34, and the beam side pin 35 are configured, as each enlarged and illustrated in FIG. 1, such that each of the pressing side pins 34, and the beam side pin 35 fits in a corresponding one of recessed portions 31a, 32a, 32b, and 20b formed in the base portion 31, the pressing member 20, or the load transfer beams 32. Thus, each pin is not displaced, and therefore, a load can be reliably transferred and assembling is simplified. Also, a pair of the base side pins 33, a pair of the pressing side pins 34, and the beam side pin 35 are disposed symmetrically about the load detection section 22a of the load cell 22 as a center.

Next, an example of a tension measurement method using the tension measurement device 1 according to this embodiment will be described.

First, as illustrated in FIG. 6, the fastening belt B is placed on the pair of the first support rollers 10 such that the first case 3 and the second case 4 are opened with the hinge portion 2 as a center to clamp the fastening belt B with the second case 4. Thus, it is not needed to have the fastening belt B pass around the pressing member 20, and therefore, the fastening belt B can be clamped by the first case 3 and the second case 4 with the fastening belt B set, thereby easily performing tension measurement.

Next, the clamping rod 5 is caused to slide with the sliding axis 6 as a center to fit in the rod housing section 4a provided in the second case 4 and the knob 7 is turned to be lightly tightened. Then, the fastening adjusting section 13 is operated to tighten the fastening belt B by the pair of first support rollers 10 with a proper force. Thus, even when a thickness of the fastening belt B is changed, the fastening belt B can be pressed by the pair of first support rollers 10 with a proper force.

Then, while checking a tension via the display section 24, additional tightening of a subject to be fastened or the like by the fastening belt B is performed. As described above, the tension of the fastening belt B can be measured while the fastening belt B is fastened, and tension management is very easy.

Figure 9:
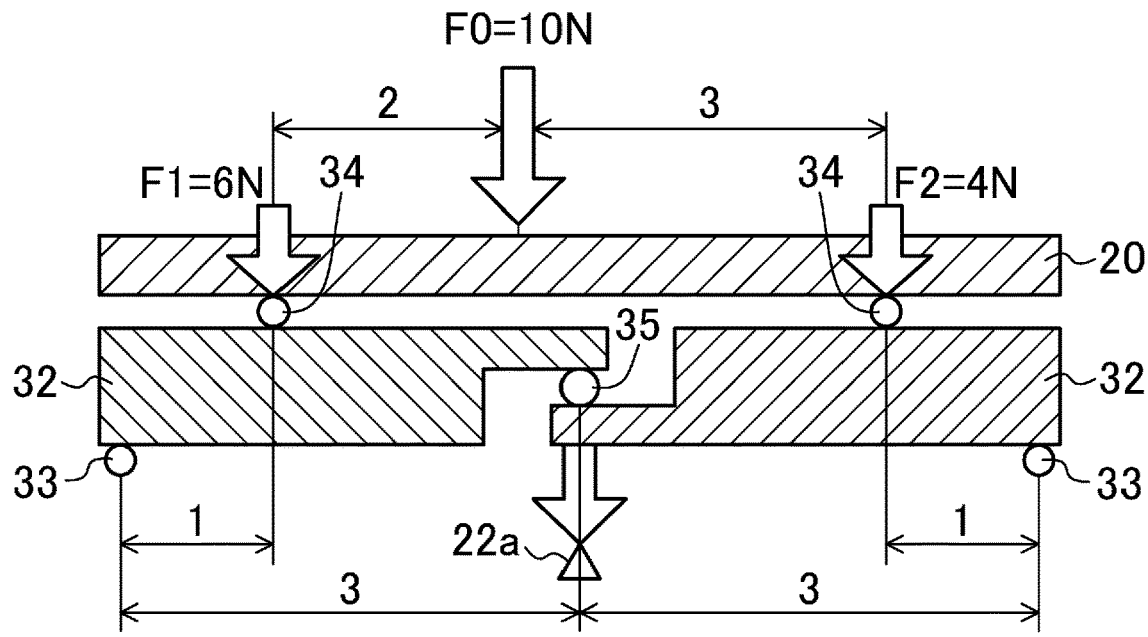
FIG. 9 is a view illustrating how a load applied to a load measurement device is transmitted.

For example, in FIG. 9, as illustrated horizontally inverted from the view of FIG. 1, a case in which a position of the fastening belt B is shifted in one direction and a load F0=10N is applied to a position to which a load center is shifted, that is, a position located at 2:3, is assumed. In this case, a load applied to the pressing side pins 34 is divided such that divided loads are F1=6N and F2=4N.

Assuming that, when viewed from each of the base side pins 33, a positional relationship with the corresponding pressing side pin 34 and the beam side pin 35 is 1:3 in each of right and left portions, a load F3 that is transferred to the beam side pin 35 is F3=6N/3+4N/3=10/3N=3.33N.

Figure 10:
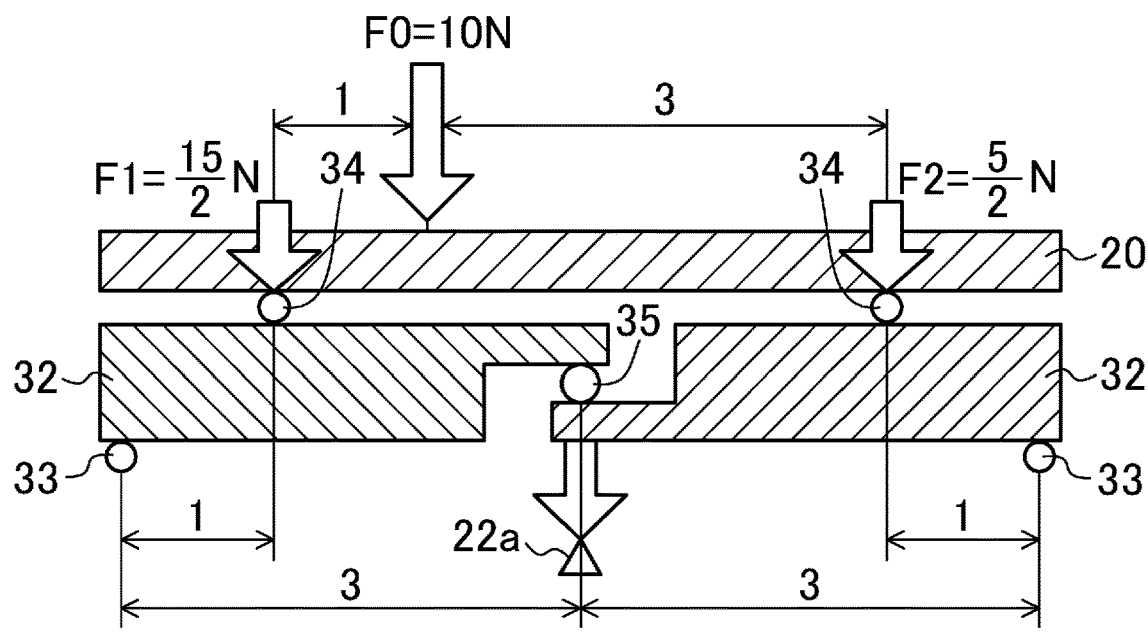
FIG. 10 is a view illustrating how a load applied to a different portion of the load measurement device is transferred.

Similarly, as illustrated in FIG. 10, a case in which the position of the fastening belt B is shifted in one direction and a load F0=10N is applied to a position to which the load center is shifted, that is, a position located at 1:3, is assumed. In this case, the load applied to the pressing side pins 34 is divided such that divided loads are F1=15N/2 and F2=5N/2.

Assuming that, similar to FIG. 9, when viewed from each of the base side pins 33, a positional relationship with the corresponding pressing side pins 34 and the beam side pin 35 is 1:3 in each of right and left portions, the load F3 that is transferred to the beam side pin 35 is F3=5N/2+5N/6=3.33N, which is equal to that in FIG. 9. That is, even when the position to which the load F0 is applied is shifted, the measurement result is the same. Also, compared to a case in which a force is directly transferred to the load cell 22, the load is ⅓. As described above, in this embodiment, the load F3 applied to the load cell 22 can be reduced to be smaller than the actual load F0 and a ratio at which the load F3 is reduced can be arbitrarily selected by adjusting disposition of each pin. In this embodiment, an actual value can be estimated by multiplying a measured value that has been obtained by three. In this embodiment, the pair of second support rollers 21 is provided in opposite positions to the pair first support rollers 10 that support the fastening belt B such that the fastening belt B is clamped between the support rollers 10 and 21, and therefore, even when the thickness of the fastening belt B is changed, a contact angle is hardly changed and variations of the tension can be reduced. Also, in this embodiment, the pressing member 20 is configured to properly project, and thereby, a tension can be measured from a component force applied to the pressing member 20. Also, the positional relationship between the pressing member 20 and the pair of second support rollers 21 is fixed, and thereby, even when the thickness of the fastening belt B is changed, a contact angle θ of the pressing member 20 with respect to the fastening belt B is hardly changed. Therefore, the tension of the fastening belt B can be accurately measured.

As has been described above, in this embodiment, even when a load position in which a load is applied to the pressing member 20 is shifted from the load cell 22, the load is transferred to the load cell 22 via the pair of load transfer beams 32, and therefore, a measurement error is reduced by actions of two levers. Also, because the load is transferred by each pin, a linear motion structure is not needed and a space-saving structure can be achieved, so that the load applied to the pair of load transfer beams 32 in a narrow space is reliably transferred to the load cell 22.

Therefore, with the tension measurement device 1 according to this embodiment, a biased load applied to the load detection section depending on the setting position of the fastening belt B can be reduced by using the principle of leverage and the measurement error can be reduced.

OTHER EMBODIMENTS

According to the present disclosure, the above described embodiment may be implemented as the following structure.

That is, in the above described embodiment, the member to be measured is the fastening belt B that is used for packing or the like, but the present disclosure can be applied to a transmission belt or a conveyance belt.

Note that the above described embodiment is merely an essentially preferred example and is not intended to be particularly limiting the present disclosure, application of the present disclosure, and the scope of use.

What is claimed is:
1. A tension measurement device, comprising:
a load sensor;
a base portion in which the load sensor is provided;
a pair of load transfer beams each having a support point and an action point provided in different positions and being configured to transfer a load to the load sensor at a tip side;
a pressing member which is supported by the action points of the pair of load transfer beams and to which the load is applied; and
a pair of rotatable first support rollers disposed at both sides of the pressing member,
wherein
a subject member to be measured is clamped between the pair of first support rollers and the pressing member, and thereby, a tension can be measured.
2. The tension measurement device of claim 1, wherein the pair of load transfer beams has a plate-like shape and is supported by base side pins at support points with respect to the base portion.
3. The tension measurement device of claim 2, wherein the pressing member is supported by the pair of load transfer beams via pressing side pins at the action points.
4. The tension measurement device of claim 3, wherein tips of the pair of load transfer beams overlap with one another via a beam side pin and one of the tips abuts on a load detection section of the load sensor.
5. The tension measurement device of claim 4, wherein each of the base side pins, the pressing side pins, and the beam side pin fits in a corresponding one of recessed portions formed in the base portion, the pressing member, or the load transfer beams.
6. The tension measurement device of claim 4, wherein the pair of base side pins, the pair of pressing side pins, and the beam side pin are disposed symmetrically about the load detection section of the load sensor as a center.
7. The tension measurement device of claim 4, wherein the pair of base side pins, the pair of pressing side pins, and the beam side pin are disposed so as to be aligned in parallel.
8. The tension measurement device of claim 1, further comprising:
a pair of rotatable second support rollers in positions opposed to the pair of first support rollers,
wherein
the pressing member projects toward the pair of first support rollers from a line connecting the pair of second support rollers, and
a positional relationship between the pressing member and the pair of second support rollers is fixed.
9. The tension measurement device of claim 8, wherein the pair of first support rollers is rotatably supported by a first case,
the pair of second support rollers is rotatably supported by a second case,
the base portion, the pair of load transfer beams, and the pressing member are provided in the second case, and
the subject member to be measured is clamped by the first case and the second case, and thereby, a tension of the subject member to be measured can be measured.
10. The tension measurement device of claim 9, wherein the subject member to be measured is a fastening belt and, in a state in which an object is fastened by the fastening belt, the fastening belt is clamped between the first case and the second case, and thereby, a tension of the fastening belt can be measured.

* * * * *